United States Patent [19]

Gattuso et al.

[11] Patent Number: 4,734,540

[45] Date of Patent: Mar. 29, 1988

[54] CATALYST FOR THE SELECTIVE HYDROGENATION OF POLYUNSATURATED ORGANICS

[75] Inventors: Mark J. Gattuso, Palatine; Daniel L. Ellig, Des Plaines, both of Ill.

[73] Assignee: UOP Inc., Des Plaines, Ill.

[21] Appl. No.: 71,456

[22] Filed: Jul. 9, 1987

Related U.S. Application Data

[63] Continuation-in-part of Ser. No. 945,139, Dec. 22, 1986, Pat. No. 4,695,560, which is a continuation-in-part of Ser. No. 782,790, Oct. 1, 1985, abandoned.

[51] Int. Cl.$^4$ ................................................. C07C 5/05
[52] U.S. Cl. ..................................... 585/274; 585/260; 585/276; 585/277
[58] Field of Search ................ 585/260, 274, 276, 277

[56] References Cited

U.S. PATENT DOCUMENTS

| | | | |
|---|---|---|---|
| 3,472,763 | 10/1969 | Cosyns et al. ...................... | 208/255 |
| 3,726,936 | 4/1973 | Pitzer .................................. | 585/260 |
| 3,793,388 | 2/1974 | Pitzer .................................. | 585/274 |
| 4,167,529 | 9/1979 | Wideman ............................ | 585/274 |
| 4,658,080 | 4/1987 | McFarland .......................... | 585/260 |

*Primary Examiner*—Curtis R. Davis
*Attorney, Agent, or Firm*—Thomas K. McBride; John F. Spears, Jr.

[57] ABSTRACT

A process is presented which is useful for the selective hydrogenation of polyunsaturated organic compounds. The resultant product of such a reaction produces the monoolefinic equivalents of the hydrogenated polyunsaturated organic compounds. The catalyst used in this selective hydrogenation process comprises nickel and sulfur deposited on the surface of an alumina support. The preferred catalyst does not contain halogens, noble metals, alkaline earth metals, or alkali metals and is characterized by having only a very low percentage of the total pore volume being provided by pores having an average pore diameter less than 150 angstroms. The great majority of the pore volume is present in the form of macropores having diameters of 500 to 1500 angstroms.

13 Claims, 2 Drawing Figures

CATALYST FOR THE SELECTIVE HYDROGENATION OF POLYUNSATURATED ORGANICS

CROSS-REFERENCE TO RELATED APPLICATIONS

This application is a continuation-in-part of prior copending application Ser. No. 945,139 filed Dec. 22, 1986, now U.S. Pat. No. 4,695,560 which is a continuation-in-part of application Ser. No. 782,790 filed Oct. 1, 1985, now abandoned, the contents of which are incorporated herein by reference thereto.

FIELD OF THE INVENTION

The invention generally relates to a process for the selective hydrogenation of polyunsaturated organic compounds. Unique to this process is a novel catalytic composite. The invention is directly concerned with a process utilizing the composition of a solid catalyst useful in converting organic compounds containing at least one organic compound selected from the group consisting of dienes, alkynes, polyenes, and triple bonded nitriles into the corresponding monoolefinic compounds. Preferably, the process is aimed at the conversion of hydrocarbons. Such a process is employed in treating the butene feed streams to motor fuel alkylation process units and in decreasing the concentration of diolefinic hydrocarbons in the product stream from a dehydrogenation reaction. The subject invention is specifically directed to a process for the selective hydrogenation of polyunsaturated organic compounds utilizing a catalyst which consists essentially of an alumina base or support material which has a unique pore structure and has nickel and sulfur deposited upon the support material.

PRIOR ART

It has been recognized in the petrochemical and refining industries that in some instances, it is desirable to selectively convert diolefinic compounds and organic compounds containing triple bonds to monoolefinic compounds. The economic advantage of this conversion has prompted the development of a significant number of catalysts for this purpose. Many of these catalysts employ a traditional hydrogenation catalyst metal, such as nickel, platinum, and palladium, on a solid support material such as alumina. For instance, U.S. Pat. No. 3,234,298 (Langhout et al) teaches the use of a sulfided nickel on alumina catalyst for a selective hydrogenation of diene-containing cracked hydrocarbon oils. U.S. Pat. No. 3,472,763 (Cosyns et al) is pertinent for its teaching of a selective hydrogenation catalyst which comprises from 1 to 20 percent nickel as nickel oxide on alumina as a selective hydrogenation catalyst. This reference indicates that it is preferable to pretreat the catalyst with a sulfur compound and specifies preferred pore size distributions.

U.S. Pat. No. 3,662,015 (Komatsu et al) is pertinent for its teaching of a nickel on alumina selective hydrogenation catalyst. U.S. Pat. No. 4,440,956 (Couvillion) is directed to a catalyst for use in removing acetylenes from liquid hydrocarbon streams containing diolefinic hydrocarbons without substantially decreasing the percentage of diolefinic hydrocarbons in the feed material. This reference is believed pertinent for its teaching of the various aluminas which may be used in conjunction with the common hydrogenation metals in producing such a selective catalyst. U.S. Pat. No. 3,919,341 (Germanas et al) is pertinent for its teaching of a sulfided nickel on alumina composite which is basically intended to function as an olefin isomerization catalyst. However, it may be determined by reference to Table 2 and the teaching of column 12 that the test results reported therein indicate a selective hydrogenation of butadiene.

Finally, U.S. Pat. No. 4,469,907 (Araki et al) is believed pertinent for its general teaching of an improved method of selective hydrogenation, and U.S. Pat. No. 3,696,160 (Chomyn) is believed pertinent for its teaching of desirability of using selective hydrogenation upstream of or in conjunction with an alkylation process in which $C_3$ and $C_4$ olefinic hydrocarbons are consumed for the production of motor fuel.

U.S. Pat. No. 4,179,408 (Sanchez et al) describes the preparation of spherical alumina catalyst supports having a large portion of the total pore volume present in macropores greater than 1000 angstroms (columns 20–22). U.S. Pat. No. 4,179,411 (Broersma) also describes an alumina of specific pore size distribution.

BRIEF SUMMARY OF THE INVENTION

The invention is a process highly suited for the selective hydrogenation of organic compounds containing diolefinic, polyolefinic, and triple bonds to the corresponding monoolefinic compounds utilizing a novel catalyst composition. The catalyst provides outstanding selectivity in the conversion of polyunsaturated organic compounds having more than 8 carbon atoms, thereby increasing the yield of monoolefinic compounds in the product stream. The catalyst comprises an alumina support material, about 4.0 to 15 wt. % nickel and about 0.5 to 1.5 wt. % sulfur. Preferably it is essentially free of halogens and noble metals. The catalyst is characterized by a lack of micropores and an abundance of macropores. Therefore, less than 15 percent of the total pore volume of the catalyst is provided by pores having pore diameters less than 150 angstroms and more than 60 percent is provided by macropores having pore diameters greater than 600 angstroms.

DETAILED DESCRIPTION

Figure 1:
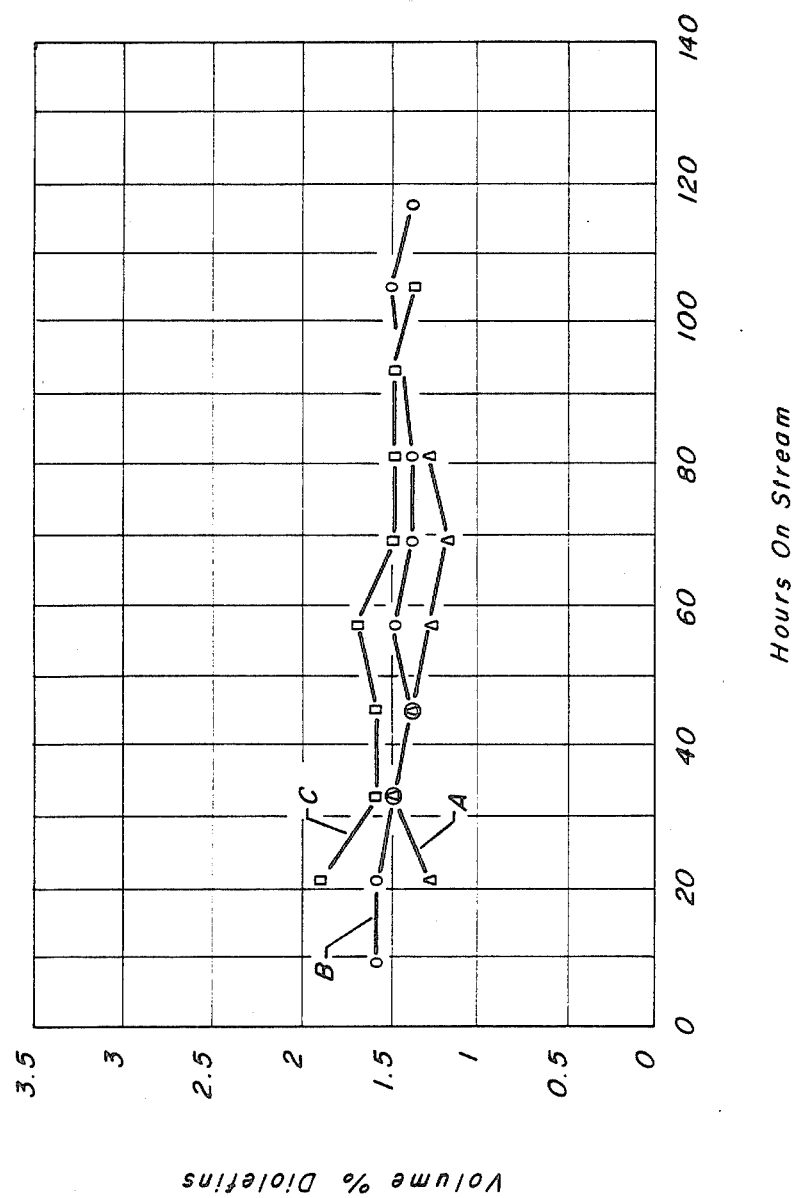
FIG. 1 is a graph presenting data on the volume percent of diolefins in the effluent stream of a pilot plant testing the subject process and two reference processes.

Many petrochemical and biological processes either produce or consume monoolefinic compounds. In many of these processes, polyunsaturated compounds are considered as impurities. As an example relating specifically to hydrocarbons, in the production of linear alkylbenzene in an integrated process such as that of U.S. Pat. No. 3,484,498, monoolefinic hydrocarbons are produced in a dehydrogenation zone and then passed into an alkylation zone. The olefins are therein reacted with benzene to produce the linear alkylaromatic hydrocarbon product. There is some unavoidable production of diolefinic hydrocarbons in the dehydrogenation zone, and these diolefinic hydrocarbons would normally be present in the olefins charged to the alkylation zone. The presence of the diolefinic straight chain material results in the production of undesirable by-products such as various biphenyl compounds. These are impurities which impart undesirable properties to the intended linear alkylbenzene product. The presence of diolefinic hydrocarbons also results in the production of undesirable high boiling point by-products and an increased rate of acid consumption. The subject selective hydrogenation process utilizing the catalyst described herein can be employed to remedy these situations and others in which polyunsaturated compounds are considered an undesired contaminant in a mixture of monoolefins and paraffins or in a substantially pure olefinic stream. The catalyst of the subject invention may also be used in a purification step performed on the effluent of an olefin separation process such as the separation of olefinic hydrocarbons from a mixture of olefinic and paraffinic hydrocarbons through the use of selective adsorption techniques.

Other applications of the instant invention include, but not limited to, the selective hydrogenation of acetylene compounds. For example, phenylacetylene, which is a by-product formed during the production of styrene, can be selectively hydrogenated to styrene. Similarly, anthracenes and alkylanthracenes, which are by-products formed during the production of detergent alkylbenzenes can be selectively hydrogenated. In addition to selective hydrogenation of these hydrocarbon compounds, process streams commonly found in food and biological processes or in the production of fertilizers and pesticides also contain polyunsaturated contaminates which can be selectively hydrogenated using the process of the instant invention. For example, it is often desired to convert triple bonded nitrogen containing compounds, such as nitriles, to imines, the double bonded equivalent compounds. This conversion can be performed using the process of the instant invention.

Accordingly, a process is presented for the selective hydrogenation of polyunsaturated organic compounds to monoolefinic organic compounds comprising contacting a feed comprising at least one organic compound selected from the group consisting of dienes, polyenes, alkynes and triple bonded nitriles in a reaction zone at selective hydrogenation conditions with a catalyst consisting essentially of an alumina support material, about 0.05 to 1.5 wt. % sulfur, and about 1.0 to 25.0 wt. % nickel, where the alumina support material is characterized by having a total pore volume greater than 1.4 but less than 2.5 cc/g, a surface area greater than 150 m$^2$/g, with less than 25 percent of the total pore volume being provided by pores having pore diameters of less than 150 angstroms and with over 60 percent of the pore volume being provided by pores having pore diameters greater than 600 angstroms to produce a product substantially free of polyunsaturated organic compounds.

The feed stream processed by the subject catalyst may comprise a mixture of different organic compounds having the same number of carbon atoms per molecule or a mixture of organic compounds having a significant range in carbon numbers. For instance, the feed stream processed with the catalyst of the subject process may contain essentially only $C_4$ or $C_5$ hydrocarbons. Alternatively, the feed stream may comprise a mixture of $C_8$ to $C_{15}$ hydrocarbons including paraffinic hydrocarbons, monoolefinic hydrocarbons, and diolefinic hydrocarbons. The term "polyunsaturated" is used herein to mean a class of organic compounds containing two or more double bonds and includes compounds having one or more triple bonds. More specifically, the term "polyunsaturated" relates to organic compounds selected from the group consisting of dienes, polyenes, alkynes, and triple bonded nitriles. In general, it is believed the subject process should be most effective in treating feed streams containing about 0.1 to about 5 wt. % of diolefinic organic compounds and/or organic compounds having at least one triple bond and having from 8 to 20 carbon atoms per molecule.

Selective hydrogenation processes are normally performed at relatively mild hydrogenation conditions. These conditions will normally result in the hydrocarbons being present as liquid phase materials. The reactants will normally be maintained under the minimum pressure sufficient to maintain the reactants as liquid phase hydrocarbons. A broad range of suitable operating pressures therefore extends from about 276 to about 5516 kPa (ga), with a pressure between about 345 to about 2069 kPa (ga) being preferred. A relatively moderate temperature between about 25° and about 350° C. should be employed. Preferably, the temperature of the hydrogenation zone is maintained between about 50° and about 200° C. The liquid hourly space velocity of the reactants through the selective hydrogenation catalyst should be above 1.0 hr$^{-1}$. Preferably, it is above 5.0 and more preferably it is between 5.0 and 35.0 hr$^{-1}$. Another variable operating condition is the mole ratio of hydrogen to polyunsaturated organics maintained within the selective hydrogenation zone. The amount of hydrogen required to achieve a certain conversion is believed dependent upon both reactor temperature and the molecular weight of the feed organic compounds. To avoid the undesired saturation of a significant amount of monoolefinic organic compounds that may be present in the feed, the hydrogen present in the reaction zone should be less than 2.0 times the stoichiometric amount required to selectively hydrogenate the polyunsaturated organics in the feed to the monoolefinic equivalents. Preferably, the mole ratio of hydrogen to polyunsaturated compounds in the material entering the bed of selective hydrogenation catalyst is maintained between 1:1 and 1.8:1. In some instances, it may be desirable to operate with a less than stoichiometrically required amount of hydrogen, with mole ratios down to 0.75:1 being acceptable. The optimum set of conditions will of course vary depending on such factors as the composition of the feed stream and the degree of saturation of the olefinic organic compounds which it is desired to perform. In any event, the product from the reaction zone will be substantially free of polyunsaturated organic compounds. The term "substantially free" means less than 1,000 ppm weight basis of diolefinic organic compounds and/or organic compounds containing triple bonds.

According to the subject process, the catalyst is preferably employed in a fixed bed reactor containing a cylindrical bed of catalyst through which the reactants move in a vertical direction. It is preferred that the reactants flow upward through the reactor as this provides good mixing. The catalyst may be present within the reactor as pellets, spheres, extrudates, irregular shaped granules, etc. To employ the catalyst, the reactants would be preferably brought up to the desired inlet temperature of the reaction zone, admixed with hydrogen and then passed into and through the reactor. Alternatively, the reactants may be admixed with the desired amount of hydrogen and then heated to the desired inlet temperature. In either case, the effluent of the reaction zone may be passed into a product recovery facility for the removal of residual hydrogen or may be passed directly into downstream product utilization zones if the presence of the residual hydrogen is acceptable. Hydrogen may be removed by flashing the effluent stream to a lower pressure or by passing the effluent stream into a stripping column.

The preferred form of the catalyst is spheres having a diameter between about 1/64 and ⅛-inch. Spheres of solid catalyst support material can be made a number of different ways including rolling and compaction techniques. However, it is greatly preferred that the spherical alumina particles are formed by a method for effecting gelation of an alumina sol such as described in U.S. Pat. No. 2,620,314 (Hoekstra). This method of gelation of alumina to form spheres is commonly known in the art as the oil drop method. The alumina sol may be also formed a number of different ways. A typical one is to digest aluminum metal with an aqueous solution of approximately 12% hydrogen chloride to produce an aluminum chloride sol. Another method comprises electrolysis of a solution of aluminum chloride in an electrolytic cell. A common method of preparing an alumina sol is the addition of aluminum metal to an aqueous solution of aluminum chloride with this mixture being subjected to heating and digesting at its boiling point. The method in which the alumina sol is prepared is not intended to be a limiting feature of the subject invention and the sol may be made by any method delivering a suitable sol. Preferably, the sol will have a weight ratio of aluminum to chloride of about 13:1 or more.

A preferred method for effecting the gelation of the sol comprises the steps of admixing the sol with a gelling agent at a temperature below the gelation temperature and then dispersing the resulting admixture as droplets in the hot oil bath whereby gelation occurs with the formation of firm spherical gel particles. The alumina hydrogel spheres are then subjected to certain aging treatments in order to impart the desired physical characteristics. Generally, a complete aging treatment comprises aging in hot oil for a period of at least 10 hours, aging in a suitable liquid alkaline medium at least 10 hours, and finally washing with water to reduce the concentration of alkaline medium. In such a process for the forming and aging of alumina particles, the hydrogel spheres are not to be contacted with water prior to being aged in the liquid alkaline medium. The spheres are water-soluble at these earlier stages of the process and can be destroyed upon contact with water. The aging treatment may be effected at a temperature of from about 49° to about 260° C. and above about 100° C., there exists a tendency for the rapid evolution of gases which cause the hydrogel spheres to rupture and otherwise become weak. By maintaining a superatmospheric pressure during the forming and aging step, higher temperatures may be employed for aging. The utilization of higher temperatures offer such advantages as the elimination of aging in a liquid alkaline solution. The spheres may therefore be washed with water immediately following the oil aging step. Typically, gelled particles are aged in the oil bath for a time of from about 1 to about 24 hours at a temperature of from about 90° to about 150° C. and at a pressure ranging from atmospheric to about 1034 kPa. If oil aged under atmospheric pressure conditions, the gelled particles are generally further aged in a dilute aqueous ammoniacal solution for 2 to 4 hours. After being aged, the particles are water washed, dried, and calcined.

The gelation of the alumina hydrosol may be effected by admixing the sol with hexamethylenetetramine (HMT), a weak base having a strong buffering action at a pH of from about 4 to about 10. This material also has an increased rate of hydrolysis at increased temperature without a sudden evolution of gas which is advantageous in the gelation procedure. It is also known that a mixture of urea and HMT may be employed as the gelling agent. Upon heating the mixture to an elevated temperature, the gelling agent decomposes and forms ammonia which causes the hydrosol to set to a gel and permits forming alumina hydrogel spheres. Following gelation and aging, the particles may be oven dried at 110° C. and then heated gradually to about 650° C. and calcined in air at this temperature for 2 hours. The resultant material after the air calcination is essentially gamma alumina. What is meant by the term "essentially" is that the resultant alumina support be comprised of at least 90 wt. % gamma alumina. To ensure that the support material be essentially gamma alumina, it is highly desirable that the support material not be exposed to a temperature in excess of 850° C. Exposure to temperatures in excess of 850° C. will result in a phase change of the alumina, converting it from the gamma- to delta-, theta-, and possibly even alpha-alumina. Such a phase change is usually accompanied by a collapse of the small pores (less than 100 angstroms) creating larger pores which results in an increase in total pore volume. However, because the surface area is directly proportional to the quantity and pore size of the small pores, the collapse of these pores results in a dramatic drop in surface area of the support material. Therefore, by utilizing the oil drop method, it is possible to form a gamma alumina support material having a total pore volume greater than 1.4 cc/g with a surface area in excess of 150 m$^2$/g, thus avoiding the attendant problems just described associated with alternative forming techniques.

Although not completely understood, utilization of the oil drop method for preparation of the alumina support material yields a superior support as compared to other forming techniques known in the art, such as, for example, extrusion. It has been found that when the oil drop method is employed, it is possible to produce alumina supports having the required total pore volume of greater than 1.4 cc/g and still maintain a high surface area of greater than 150 m$^2$/g. Other forming techniques are inadequate in that in order to achieve increased total pore volume, the supports must be heat treated, for example, by calcination. However, such treatment causes a precipitous reduction in the surface area of the support. Typically, these non-oil dropped supports cannot achieve total pore volumes of greater than 1.0 cc/g.

Further teaching on the formation of the preferred alumina spheres by the oil dropping method may be obtained by reference to U.S. Pat. Nos. 3,096,295, 3,926,849, and 4,250,058 which are expressly incorporated herein by reference. The formation of spheroidal alumina particles is also addressed in U.S. Pat. Nos. 4,179,408, 4,179,411, and 4,514,511.

Besides the basic alumina support material, there are two other components which are important to the performance of the catalyst used in the instant process. First of all, there is a nickel component, which may be present only on the outer surface of the alumina support material or uniformly throughout the support. Having the nickel on the outer surface of the support means that the nickel is surface-deposited, such that, essentially all of the nickel present on the support is concentrated within the outermost 200 micron layer of the support. The concentration of nickel in the finished catalyst is preferably between 5.0 and 15.0 wt. %, on the basis of the elemental metal. The nickel component can be added to the catalyst during the sphere formation procedure if it is so desired. However, it is greatly preferred that the nickel component of the catalyst is added to the previously formed alumina spheres as by impregnation in which the formed alumina spheres are immersed into a solution of a nickel compound. Preferably, the formed calcined alumina spheres are immersed in an aqueous solution of nickel nitrate, nickel chloride, nickel sulfate or nickel acetate, or other water-soluble nickel compound. The solution is then preferably evaporated to dryness in contact with the spheres utilizing a rotary steam evaporator. The dried particles may then be calcined at a temperature of about 150° C. for 1 hour and then at about 525° C. for 1 hour. The formed spheres may then be dried and purged with nitrogen and are preferably subjected to a reduction step in contact with a hydrogen-containing gas.

Also preferably present in significant amounts only upon the surface of the alumina support is the sulfur component of the catalyst. This component is preferably present in a concentration varying between about 0.05 to about 1.5 wt. %. A preferred range of the sulfur concentration in the subject catalyst is from 0.1 to 1.0 wt. % with it being highly preferred that the sulfur concentration in the finished catalyst is less than 0.5 wt. %. The sulfur component is preferably added to the catalytic composite in a final preparation step after the formation of an alumina base and the placement of the nickel upon the alumina base material. In this sulfiding procedure, the initial composite is subjected to sulfiding conditions sufficient to provide the desired sulfur concentration. Sulfiding may be performed under liquid phase conditions, however, it is greatly preferred to perform this step at vapor phase conditions. It is therefore preferred to effect the deposition of the sulfur component upon the catalyst by contacting the initial composite with a vaporous sulfur-containing compound. Preferably, the sulfur-containing compound is present in admixture with hydrogen. A preferred sulfur-containing or sulfur-yielding compound is hydrogen sulfide. Other sulfur or sulfide-yielding compounds which may be employed for this purpose include ammonium sulfide, ammonium hydrosulfide, the alkyl and aryl mercaptans, organic thioethers, disulfides, thioaldehydes, and other sulfur-yielding organic compounds. The sulfiding conditions will therefore preferably include a temperature sufficient to maintain the sulfiding compound present as a vapor, with these temperatures ranging from about 10° to about 500° C. A preferred range is from about 20° to about 400° C. when hydrogen sulfide is utilized as the sulfiding agent. The pressure employed during the sulfiding step can be selected from an extremely broad range and does not greatly affect the course of the sulfiding step. Atmospheric pressure is preferred. The initial composite may be sulfided statically using hydrogen sulfide or in a flowing gas stream containing about 5 to about 30% hydrogen sulfide which is passed over the initial catalyst composite at a gas hourly space velocity of about 2.5 to 10.

The preferred embodiment of the subject process is also specific as to those compounds of the catalyst which preferably are not present within the catalytic composite. The subject catalyst may therefore be characterized herein as being "essentially free" of certain elements. As used herein, the term "essentially free" is intended to indicate a lack of any intent to specifically include the specified element or grouping of elements in the catalyst. It is recognized however that due to the impurities present in industrial grade chemical supplies and also due to the contamination possible during manufacturing steps in catalyst manufacturing plants which are employed to produce a variety of different catalyst compositions, some contamination of the catalyst with undesired materials will unavoidably occur. The term "essentially free" is therefore employed herein not to indicate a total lack of the specified element or grouping of elements but to indicate that the concentration of the specified element or group of elements is less than 0.1 wt. % of the total finished catalyst.

Preferably, the catalyst is essentially free of the noble or platinum group metals, which include platinum, palladium, rhodium, and iridium. Preferably, the catalyst is essentially free of all Group VIII metals except for nickel. Therefore, the catalyst is essentially free of iron and cobalt. Furthermore, the catalytic composite is preferably essentially free of the alkaline earth metals, of which calcium, strontium, and barium are the most common. The catalytic composite should also be essentially free of the alkali metals of which lithium, sodium, and potassium are the most commonly used catalyst components. Finally, it is also preferred that the catalytic composite is essentially free of the halogens including fluorine, chlorine, bromine, and iodine.

A preferred embodiment of the subject process may therefore be characterized as a process utilizing a catalyst for the selective hydrogenation of polyunsaturated organic compounds which is essentially free of halogens and noble metals, and which comprises an alumina support material having a total surface area greater than 150 m$^2$/g, with less than 25%, preferably less than 15%, of the total pore volume of the catalyst being provided by pores having average pore diameters of less than about 300 angstroms and with over 65% of the pore volume being provided by pores having average pore diameters greater than 600 angstroms, and also comprises about 1.0 to 25.0 wt. % nickel and about 0.1 to 1.0 wt. % sulfur.

Figure 2:
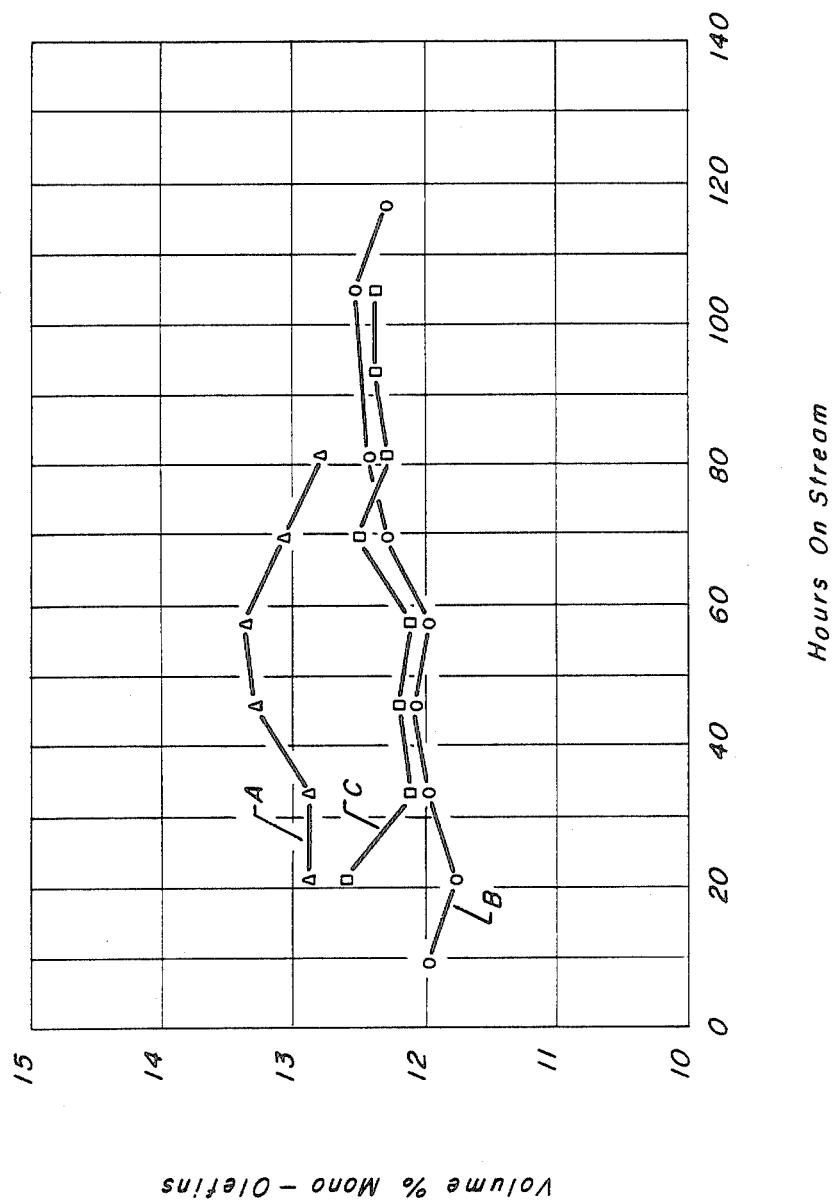
FIG. 2 is a similar graph which gives the concentration of monoolefins in the effluent stream during the same tests.

The superior performance of the subject process is demonstrated by the data provided in FIGS. 1 and 2. The data in these figures were arrived at by testing three different processes at identical conditions in the same pilot plant to determine their effectiveness for the selective hydrogenation of diolefinic hydrocarbons present in a feed stream comprising an admixture of paraffinic and olefinic hydrocarbons. The feed stream is believed representative of that which would be produced by a commercial dehydrogenation process consuming a feed material consisting of $C_{10}$ to $C_{13}$ hydrocarbons. The feed stream contained about 0.99 vol. % aromatics, with the aliphatic portion of the feed stream comprising 0.1 vol. % $C_9$'s, 11.2 vol. % $C_{10}$'s, 26.5 vol. % $C_{11}$'s, 34.5 vol. % $C_{12}$'s, 27.6 vol. % $C_{13}$'s, and 0.1 vol. % $C_{14}$'s. The feed stream contained a total of 85.46% saturates, 11.46% monoolefins, and 2.09% diolefins. The remainder of the feed stream consisted of non-normal hydrocarbons. The feed stream was first stored in a feed tank under a pressurized atmosphere of high purity hydrogen until the feed liquid was saturated with hydrogen. In trials, the feed stream was then contacted with the different catalyst at a liquid hourly space velocity of 5.0 at a temperature of 200° C. and at a pressure of 689 kPa (ga). The effluent of the pilot plant was periodically sampled and analyzed to provide the information plotted on FIGS. 1 and 2. It should be noted that the time on-stream plotted along the X-axis or abscissa on the figures is actually time measured after the catalyst had been on-stream for a total of 552 hours.

Each process utilized a different catalytic composition. The compositions of the three catalysts tested in the processes according to the procedure just described is given in the following Table. Process A corresponds to the subject preferred process. Process B is not in accordance with the invention because it utilized an alumina support material having a pore volume of less than 1.4 cc/g. In Process C, likewise not in accordance with the invention, its catalyst is based on an extruded base material comprising an admixture of 85 wt. % alumina and 15 wt. % clay. As may be seen by FIG. 1, the process of the instant invention, Process A, produces a treated hydrocarbon effluent which has a lower concentration of diolefinic hydrocarbons than Processes B and C, which utilize catalysts that contain similar amounts of nickel and which have been sulfided in a similar manner. It is however more important to direct attention to the information provided in FIG. 2 which indicates that the subject process is more effective at producing a higher concentration of the desired monoolefins than the two comparison processes. By a comparison of the information provided by FIGS. 1 and 2, it may be observed that Process A is much more selective at only effecting the hydrogenation of diolefinic hydrocarbons as compared to Processes B and C. The results are clearly indicative of Processes B and C effecting the hydrogenation of monoolefinic hydrocarbons present in the feedstream in addition to hydrogenation of diolefinic hydrocarbons. It is therefore evident that a process of the instant invention would result in higher yields of the desired product whether this product is simply the monoolefinic hydrocarbon or is a product which results from the consumption of the monoolefinic hydrocarbon such as an alkylation process for the production of linear alkylbenzene.

By referring to the Table, it may be seen that the catalyst composition utilized in Process A is unique in its pore size distribution. Specifically, it has a much lower percentage of the total pore volume present in micropores (less than 300 angstroms) and most of its pore volume present in macropores (greater than 600 angstroms). It may be observed that most of the macropore volume is in pores less than 1500 angstroms in diameter. In comparison, the catalysts utilized in comparison Processes B and C have significant percentages of their pore volume present as micropores. The catalyst of the preferred process also differs in having a total pore volume which is much larger than the catalysts of the reference processes.

The finished catalyst of the subject invention should have a total pore volume greater than 1.2 cc/g. Preferably, the catalyst will have a pore volume greater than 1.4 cc/g but less than 2.5 cc/g. As previously stated, less than 25%, and preferably less than 20%, of this volume is to be provided by pores having an average pore diameter as measured by mercury intrusion of less than 150 angstroms. Preferably, less than 30% of the total volume is provided by pores having an average diameter less than 300 angstroms. The preference for a large amount of macropores is shown by the requirement that over 65% is provided by pores having an average diameter greater than 500 angstroms. Preferably, this 65% or greater portion is provided by pores having an average pore diameter greater than 600 angstroms. The presence of a few exceptionally large pores which would provide this amount of volume is not preferred. Rather, the size distribution of the macropores of the subject catalyst is preferably rather narrow. Pores having pore diameters between 500 and 1500 angstroms should account for at least 50% of the total pore volume. More preferably, 60% of the total pore volume is provided by these macropores having mean pore diameters between 600 and 1500 angstroms.

TABLE

| | Catalyst Properties | | |
|---|---|---|---|
| Process | A | B | C |
| Base Composition | Alumina | Alumina | Alumina + clay |
| Ni, wt. % | 9.5 | 9.9 | 9.6 |
| S, wt. % | 0.27 | 0.10 | 0.22 |
| Surface Area, m²/g | 174 | 195 | 262 |
| Total Pore Volume, cc/g | 1.63 | 0.732 | 0.882 |
| % Pore Volume in Pores | | | |
| >1500 angstroms | 1.47 | 0.34 | 20.0 |
| >1000 angstroms | 46.2 | 0.34 | 22.1 |
| >600 angstroms | 65.9 | 1.16 | 24.5 |
| >500 angstroms | 67.3 | 1.38 | 25.4 |
| >300 angstroms | 79.0 | 2.9 | 29.9 |
| >150 angstroms | 85.5 | 26.0 | 43.6 |

What is claimed is:

1. A process for the selective hydrogenation of polyunsaturated organic compounds to monoolefinic organic compounds comprising contacting a feed comprising at least one organic compound selected from the group consisting of dienes, polyenes, alKynes, and triple bonded nitriles in a reaction zone at selective hydrogenation conditions with a catalyst consisting essentially of an alumina support material, about 0.05 to 1.5 wt. % sulfur, and about 1.0 to 25.0 wt. % nickel, where the alumina support material is characterized by having a total pore volume greater than 1.4 but less than 2.5 cc/g, a surface area greater than 150 m²/g, with less than 25 percent of the total pore volume being provided by pores having pore diameters of less than 150 angstroms and with over 60 percent of the pore volume being provided by pores having pore diameters greater than 600 angstroms to produce a product substantially free of polyunsaturated organic compounds.

2. The process of claim 1 further characterized in that the feed contains from about 0.1 to about 5 wt. % diolefinic compounds.

3. The process of claim 1 further characterized in that the feed contains from about 0.1 to about 5 wt. % organic compounds having triple bonds.

4. The process of claim 1 further characterized in that the feed is maintained as liquid phase in the reaction zone.

5. The process of claim 1 further characterized in that the selective hydrogenation conditions comprise a temperature of from about 50° to about 200° C., a pressure from about 345 to about 2069 kPa (ga), and a liquid hourly space velocity of from about 5 to about 35 hr$^{-1}$.

6. The process of claim 2 further characterized in that the reaction zone contains less than 2.0 times the stoichiometric amount of hydrogen required for conversion of the polyunsaturated organic compounds to the corresponding monoolefins.

7. The process of claim 1 further characterized in that the feed contains a mixture of organic compounds having from 8 to 20 carbon atoms per molecule.

8. The process of claim 1 further characterized in that the feed contains $C_4$ hydrocarbons.

9. The process of claim 1 further characterized in that the feed contains $C_5$ hydrocarbons.

10. The process of claim 1 further characterized in that less than 15 percent of the total pore volume of the catalyst is provided by pores having an average pore diameter of less than 300 angstroms.

11. The process of claim 1 further characterized in that the catalyst contains less than 0.5 wt. % sulfur.

12. The process of claim 1 further characterized in that less than 20 percent of the total pore volume of the catalyst is provided by pores having pore diameters less than 150 angstroms.

13. The process of claim 4 further characterized in that at least 60 percent of the total pore volume of the catalyst is provided by macropores having mean pore diameters between 600 and 1500 angstroms.

* * * * *